United States Patent [19]
Knight

[11] Patent Number: 5,776,378
[45] Date of Patent: Jul. 7, 1998

[54] METHOD AND MEANS FOR APPLYING SCENT TO CLOTHING

[75] Inventor: William A. Knight, Centerville, Iowa

[73] Assignee: Modern Muzzleloading, Inc., Centerville, Iowa

[21] Appl. No.: 755,786

[22] Filed: Nov. 18, 1996

[51] Int. Cl.[6] .................................................. B01F 3/04
[52] U.S. Cl. ............................ 261/30; 34/104; 34/202; 34/218; 261/DIG. 65
[58] Field of Search ................. 312/31, 31.2, 31.01; 261/30, DIG. 65; 34/104, 202, 218; 239/57

[56] References Cited

U.S. PATENT DOCUMENTS

| | | | |
|---|---|---|---|
| 1,647,277 | 11/1927 | Davis | 34/202 |
| 1,828,535 | 10/1931 | Kass | 239/57 |
| 2,139,404 | 12/1938 | Evans | 239/57 |
| 2,465,362 | 3/1949 | Elliott | 34/104 |
| 2,753,164 | 7/1956 | Miller | 312/31 |
| 2,967,023 | 1/1961 | Huckabee . | |
| 3,432,939 | 3/1969 | Eichholz | 34/218 |
| 3,475,828 | 11/1969 | Feldman et al. | 34/104 |
| 4,136,464 | 1/1979 | Hay | 34/104 |
| 4,346,059 | 8/1982 | Spector . | |
| 4,511,495 | 4/1985 | Melville . | |
| 4,559,903 | 12/1985 | Bloom et al. | 34/202 |
| 4,609,245 | 9/1986 | Sakschek . | |
| 4,722,477 | 2/1988 | Floyd . | |
| 4,913,034 | 4/1990 | Ripple et al. . | |
| 5,199,188 | 4/1993 | Franz | 34/104 |
| 5,539,930 | 7/1996 | Sesselmann | 2/243.1 |
| 5,585,107 | 12/1996 | Vickers | 424/402 |

OTHER PUBLICATIONS

Kaden, "Outdoor Life", v176, p. 46(2), Aug. 1985.

*Primary Examiner*—Tim R. Miles
*Attorney, Agent, or Firm*—Zarley, McKee, Thomte, Voorhees & Sease

[57] ABSTRACT

An apparatus for applying scent to clothing has an enclosed compartment having a top, bottom and side walls. A horizontal perforated shelf extends across the compartment and divides the compartment into upper and lower portions. A closeable access opening is located in the side walls of the compartment for placing articles of clothing on top of the shelf. An air circulation conduit connects the upper and lower portions of the compartment. A fan is connected to the conduit for moving air therethrough from the upper portion to the lower portion of the compartment. A scent cartridge is in communication with the compartment in the path of air passing therethrough so the passing air will pick up the scent of the scent cartridge whereupon the scented air will move into the lower portion of the compartment, thence through the shelf and articles of clothing, and thence into the upper portion of the compartment and back into the conduit. The method of applying a scent to articles of clothing comprises placing a garment to be scented on a perforated shelf within a closed compartment, dividing the compartment into upper and lower portions, and then circulating scented air upwardly through the shelf and the garment. The scented air is then recirculated and exposed to a scented material, and the recirculation continues for a sufficient period of time that the appropriate level of scent has been imparted to the articles of clothing.

10 Claims, 4 Drawing Sheets

METHOD AND MEANS FOR APPLYING SCENT TO CLOTHING

BACKGROUND OF THE INVENTION

Most big game animals have a keen sense of smell that enables them to detect the presence of hunters at long distances. The sense of smell of these animals is their principal means of defense against hunters, and is far more sensitive than their sense of sight.

As a result, hunters often will attach scented patches or attachments to their clothing to mask their human smell. This is quite ineffective in that it does not cover a sufficient area of the total clothing to mask the human smell. Furthermore, the patches or the like are often prescented. Unless the masking scent matches the smell of the terrain in which the animals are located, this type of masking is ineffective.

It is therefore a principal object of this invention to provide a method and means for applying scent to hunting clothing that can be quickly and easily utilized in the field with any desired scent.

This and other objects will be apparent to those skilled in the art.

SUMMARY OF THE INVENTION

An apparatus for applying scent to clothing has an enclosed compartment having a top, bottom and side walls. A horizontal perforated shelf extends across the compartment and divides the compartment into upper and lower portions. A closeable access opening is located in one of the walls of the compartment for placing articles of clothing on top of the shelf. An air circulation conduit connects the upper and lower portions of the compartment.

A fan is connected to the conduit for moving air therethrough from the upper portion to the lower portion of the compartment. A scent cartridge is in communication with the compartment, and preferably in the conduit, in the path of air passing therethrough so the passing air will pick up the scent of the scent cartridge whereupon the scented air will move into the lower portion of the compartment, thence through the shelf and articles of clothing, and thence into the upper portion of the compartment and back into the conduit.

The method of applying a scent to articles of clothing comprises placing a garment to be scented on a perforated shelf within a closed compartment dividing the compartment into upper and lower portions, and then circulating scented air upwardly through the shelf and the garment. The scented air is then recirculated and exposed to a scented material, and the recirculation continues for a sufficient period of time that the appropriate level of scent has been imparted to the articles of clothing.

DESCRIPTION OF THE PREFERRED EMBODIMENT

Figure 1:
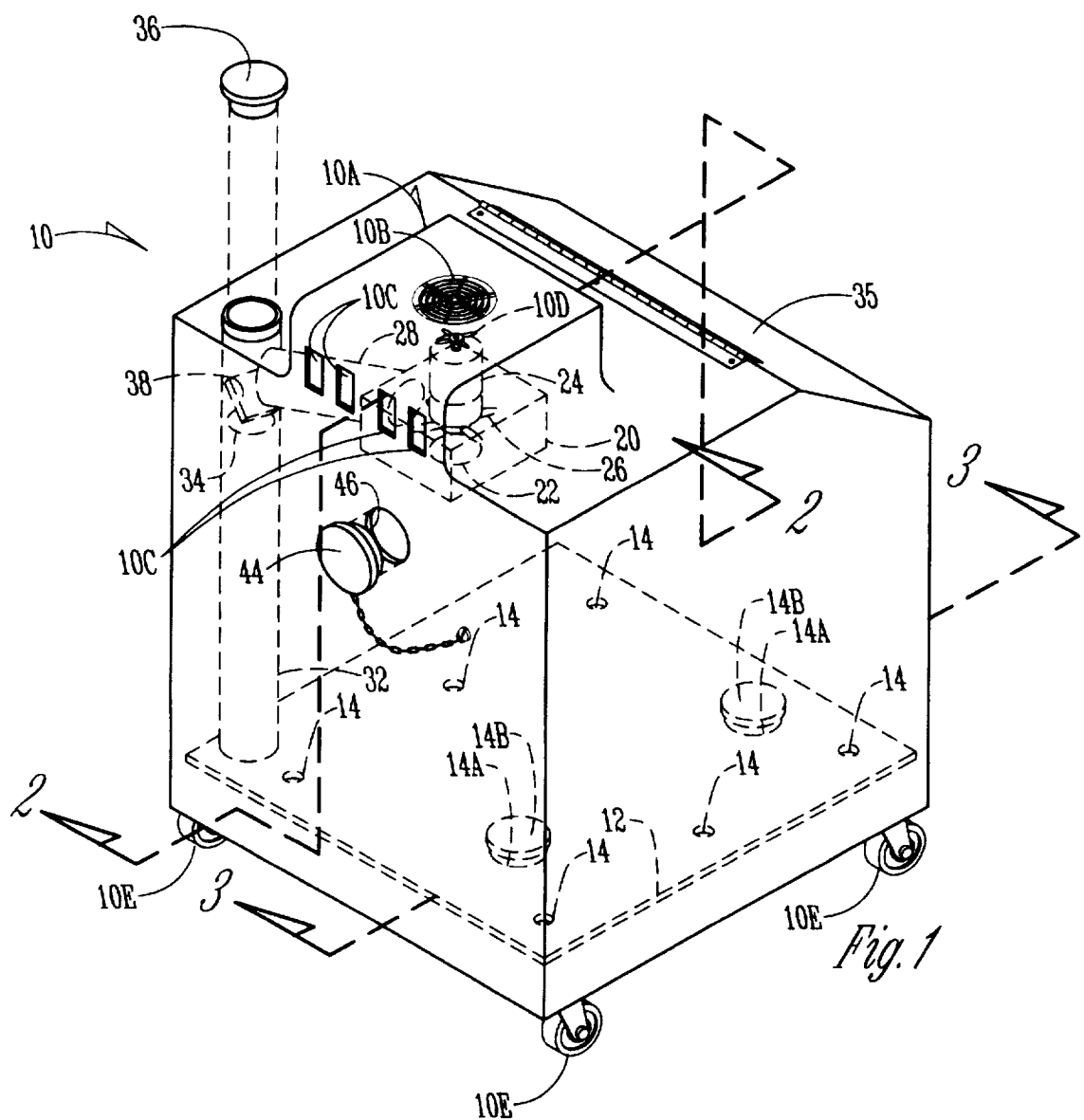
FIG. 1 is a perspective view of the device of the invention.
Figure 2:
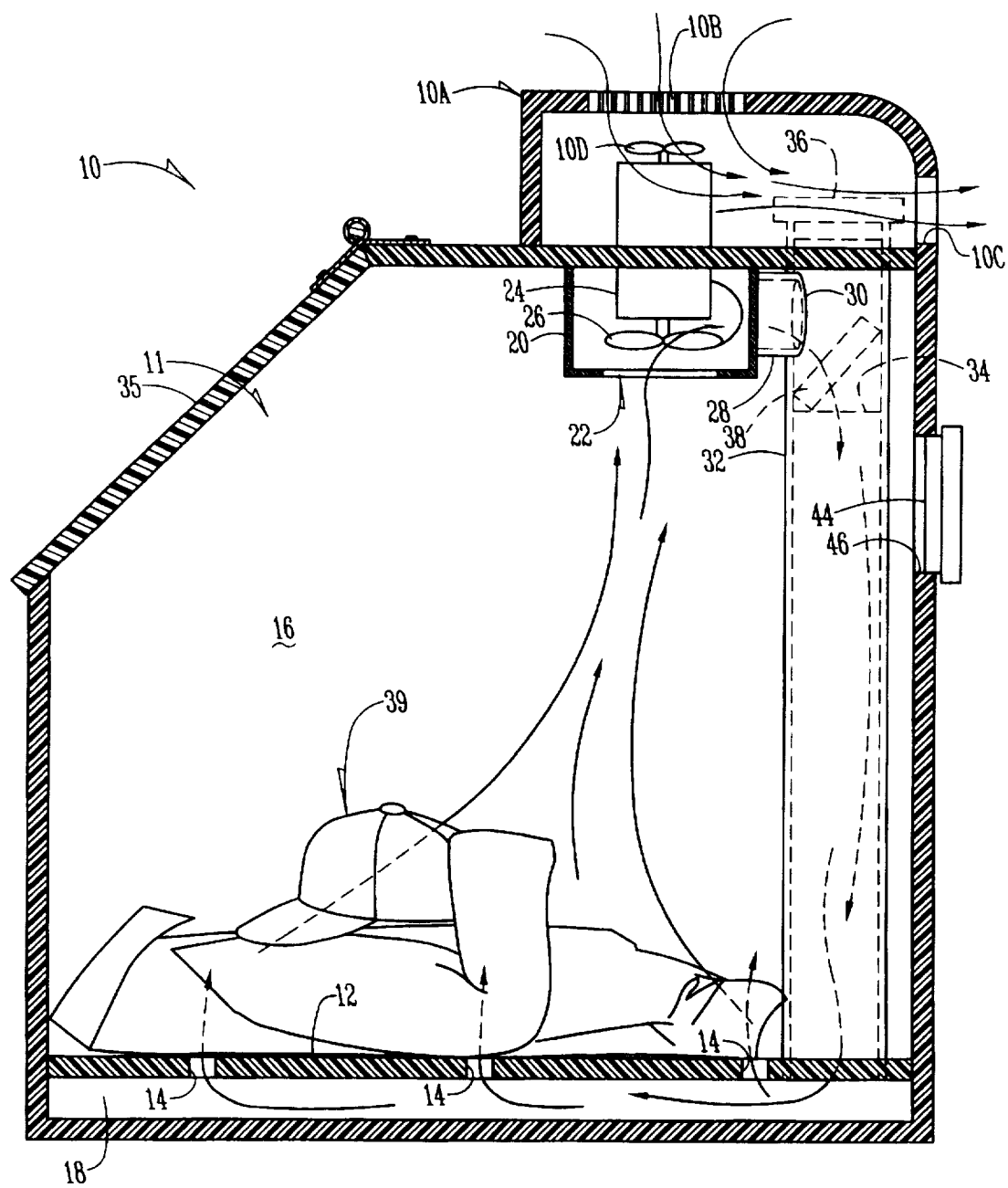
FIG. 2 is a vertical sectional view taken on line 2—2 of FIG. 1.

The housing 10 has an interior compartment 11 therein. A horizontal shelf 12 is positioned within compartment 11 and has a plurality of perforations 14 therein. A shelf 12 divides the compartment 11 into an upper portion 16 and a lower portion 18. Upper portion 16 is connected to the fan housing 20 by port 22. A conventional fan motor 24 is partially mounted within housing 20, and the fan blade 26 on motor 24 causes air to move from the motor housing 20 through passage 28 into exit port 30. An elongated conduit 32 has one of its ends secured to exit port 30, with the other end extending through shelf 12 to be in communication with the lower portion 18 of compartment 11.

A scent cartridge housing 34 is imposed in conduit 32 and has a removable cap 36 thereon. A conventional scent cartridge 38 can be selectively imposed within the housing 34.

The upper end of motor housing 24 extends through the top of housing 10 into sub-housing 10A thereon. Air inlet port 10B is located in the top of housing 10A, and exit ports 10C are located in the back side thereof. Fan blade 10D opposite to blade 26 draws cooling air in port 10B, around the upper end of motor 24, and the air then exits through exit ports 10C. Wheels 10E support housing 10.

In operation, the clothing to be scented can be placed on shelf 12 through access door 35 (FIG. 1). The fan motor 24 can be actuated either by a battery pack or through connection to a 110 volt outlet so as to force air within the compartment 11 through passage 28, exit port 30, and thence through conduit 32. As the air moving downwardly through conduit 32 passes through housing 34, it picks up the scent from cartridge 38, and the scented air then moves into the lower portion 18 of compartment 11. The scented air then moves upwardly through perforations or ports 14 in shelf 12, thence through the clothing 39, and thence back to the place of beginning in motor housing 20. Typically, in 60 seconds or so, the clothing is fully impregnated with the scent from cartridge 38.

Figure 3:
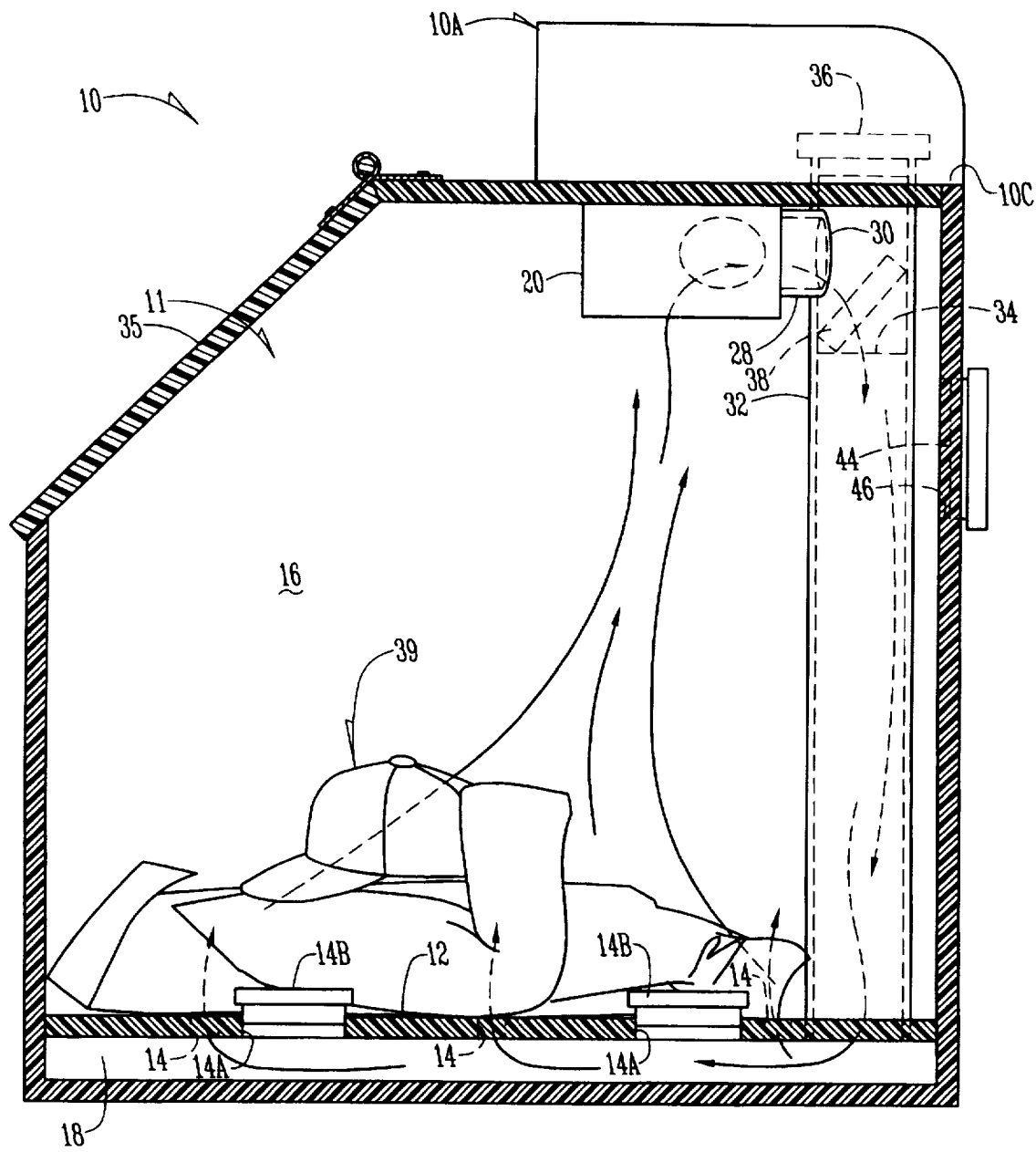
FIG. 3 is a vertical sectional view taken on line 3—3 of FIG. 1.
Figure 4:
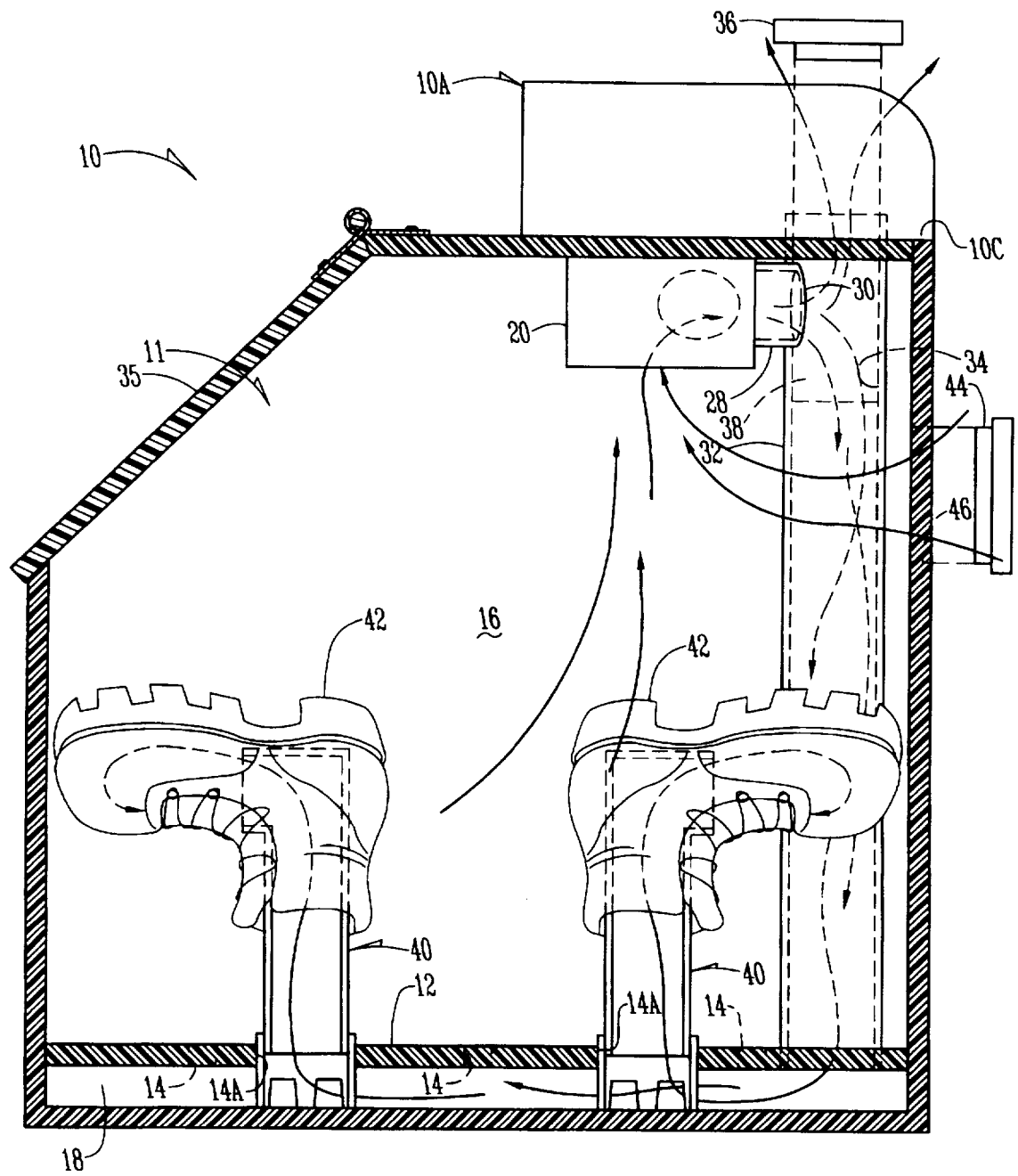
FIG. 4 is a vertical schematic view similar to FIG. 3 which shows an alternative form of the invention.

In the alternate mode of operation shelf 12 has only two aperatures 14A therein, with removable caps 14B resting therein. When it is desired to dry a hunter's footwear, the caps 14B are removed from the aperatures 14A. An upstanding post 40 which is hollow is then inserted into aperatures 14A (FIG. 3). The hunter's wet boots 42 can be inserted into the upper compartment 16 and turned upside down over the post 40. The cap 36 is removed. Cap 44 is removed from port 46 to provide a fresh air source. The operation of fan 24 will cause air to enter port 46, and then be propelled by fan blade 26 through conduit 28. Some of the air will exhaust upwardly through the upper end of conduit 32, with a portion moving downwardly in conduit 32 to the lower portion 18 of compartment 11, through perforations 14A, and through the posts 40 into the interior of the boots. This structure is particularly adaptable for drying out wet boots at the end of the day. If any undesirable odors are connected with the boots, a scent cartridge 38 can be used in this alternate form of the invention.

From the foregoing, it is seen that this invention will achieve at least all of its stated objectives.

What is claimed is:

1. A device for applying scent to clothing, comprising,
an enclosed compartment having a top, bottom, and side walls.
a horizontal perforated shelf extending across said compartment and dividing said compartment into an upper portion and lower portions,
a closable access opening in said compartment for placing articles of clothing on top of said shelf,
an air circulation conduit connecting said upper and lower portions of said compartment, fan means connected to said conduit for moving air therethrough from said upper portion to said lower portion of said compartment, a scent cartridge in communication with said compartment and in the path of air passing threrethrough so that said passing air will pick up the scent of said scent cartridge whereupon the scented air will move into the lower portion of said compartment, thence through said shelf and articles of clothing thereon, and thence into said upper portion of said compartment and back into said conduit.

2. The device of claim 1 wherein said scent cartridge means is imposed in said conduit.

3. The device of claim 1 wherein said conduit has a removable cap so that different selected scent cartridges can be placed therein.

4. A device for drying boots comprising:

an enclosed compartment having a top, bottom, and side walls, a horizontal perforated shelf extending across said compartment and dividing said compartment into the upper portion and lower portions, an air circulation conduit connecting said upper and lower portions of said compartment, fan means connected to said conduit for moving air therethrough from said upper portion to said lower portion of said compartment, a scent cartridge housing in said conduit, said shelf having at least one perforation therein, a hollow upstanding post removably mounted on said shelf and extending upwardly over said perforation, and a closeable access opening in said compartment for placing an inverted boot over the upper end of said post to cause air to flow into the interior of said boot, said post being so located in said compartment, and said compartment being of sufficient size so that a boot supported on said post can be totally enclosed within said compartment.

5. The method of applying a scent to an article of clothing, comprising, placing a garment to be scented into a compartment on a perforated shelf dividing the compartment into upper and lower portions, and circulating scented air upwardly through said shelf and said garment.

6. The method of claim 5 wherein said scented air is recirculated after passing through said garment back to said lower portion of said compartment, and thence back through said shelf and said garment.

7. The method of claim 6 wherein said recirculated air is exposed to a scented material as the scented air is being recirculated.

8. The method of applying a scent to an article of clothing, comprising, placing a garment to be scented into a compartment on a perforated shelf dividing the compartment into upper and lower portions, and circulating scented air through said shelf and said garment.

9. A device for treating clothing, comprising, an enclosed compartment having a top, bottom, and side walls, a horizontal perforated shelf extending across said compartment and dividing said compartment into an upper portion and lower portions, a closable access opening in said compartment for placing articles of clothing on top of said shelf, an air circulation conduit connecting said upper and lower portions of said compartment, fan means connected to said conduit for moving air therethrough from said upper portion to said lower portion of said compartment, an air treating substance having a scent associated with said compartment and in the path of air passing therethrough so that said passing air will pick up the scent of said air treating substance whereupon the scented air will move into the lower portion of said compartment, thence through said shelf and articles of clothing thereon, and thence into said upper portion of said compartment and back into said conduit.

10. A device of the class as described, an enclosed compartment having a top, bottom, and side walls, a horizontal perforated shelf extending across said compartment and dividing said compartment into an upper portion and lower portions, a closable access opening in said compartment for placing articles of clothing on top of said shelf, an air circulation conduit connecting said upper and lower portions of said compartment, fan means connected to said conduit for moving air therethrough from said upper portion to said lower portion of said compartment, an air scent enhancing cartridge in communication with said compartment and in the path of air passing therethrough so that said passing air will have its scent modified whereupon such air will move into the lower portion of said compartment, thence through said shelf and articles of clothing thereon, and thence into said upper portion of said compartment and back into said conduit.

* * * * *